(12) United States Patent
Behnam

(10) Patent No.: US 7,094,804 B2
(45) Date of Patent: Aug. 22, 2006

(54) WATER FREE UBIQUINONE CONCENTRATE

(75) Inventor: Dariush Behnam, Rossdorf (DE)

(73) Assignee: AQUANOVA German Solubilisate Technologies, Darmstadt (DE)

(*) Notice: Subject to any disclaimer, the term of this patent is extended or adjusted under 35 U.S.C. 154(b) by 333 days.

(21) Appl. No.: 10/276,328

(22) PCT Filed: Jun. 29, 2002

(86) PCT No.: PCT/EP02/07195

§ 371 (c)(1),
(2), (4) Date: Nov. 26, 2002

(87) PCT Pub. No.: WO03/007907

PCT Pub. Date: Jan. 30, 2003

(65) Prior Publication Data

US 2003/0165438 A1 Sep. 4, 2003

(30) Foreign Application Priority Data

Jul. 12, 2001 (DE) .................................. 101 33 305

(51) Int. Cl.
*A61K 31/35* (2006.01)
(52) U.S. Cl. ........................ 514/460; 514/690
(58) Field of Classification Search ............ 514/460, 514/690
See application file for complete search history.

(56) References Cited

U.S. PATENT DOCUMENTS

| | | | |
|---|---|---|---|
| 6,048,566 A | 4/2000 | Behnam et al. | |
| 6,056,971 A | 5/2000 | Goldman | |
| 6,200,550 B1 * | 3/2001 | Masterson et al. | ............ 424/49 |
| 6,300,377 B1 | 10/2001 | Chopra | |

FOREIGN PATENT DOCUMENTS

| | | |
|---|---|---|
| DE | 3224619 | 5/1983 |
| DE | 10104847 | 12/2001 |
| DE | 10133305 | 2/2003 |
| EP | 0023349 | 2/1981 |
| EP | 0179583 | 4/1986 |
| EP | 0196085 | 10/1986 |
| EP | 0617957 | 10/1994 |
| EP | 1249230 | 10/2002 |
| JP | 55081813 | 6/1980 |
| JP | 60/199814 A | 10/1985 |
| JP | 62/123113 A | 6/1987 |
| WO | 9821984 | 4/2000 |
| WO | 0152822 | 7/2001 |

OTHER PUBLICATIONS

BTS046/03 Final Report, "Comparative bioavailabilty of a water and a fat soluble coenzyme $Q_{10}$ formulation in healthy volunteers", conducted by BioTeSys GmbH, pp. 1-29.

Kommuru et al., "Self-emulsifying drug delivery systems (SEDDS) of coenzyme $Q_{10}$: formulation development and bioavailability assessment"; Elsevier International Journal of Pharmaceutics, vol. 212, pp. 233-246, 2001.

Weis, et al., "Bioavailability of Four Oral Coenzyme $Q_{10}$ Formulations in Healthy Volunteers", Molec. Aspects Med., vol. 15 (Suppl.), pp. 273-280, 1994.

* cited by examiner

*Primary Examiner*—Jean C. Witz
(74) *Attorney, Agent, or Firm*—Jacobson Holman PLLC

(57) ABSTRACT

A water soluble, essentially water-free ubichinon concentrate is described, which contains an emulsifier with an HLB value between 9 and 16, ubichinon $Q_{10}$, as well as a light oil containing triglyceride. Furthermore, a method for producing the concentrate is described.

23 Claims, 4 Drawing Sheets

FIGURE 2

Method of Manufacture of an emulsion
(Inversion due to thermal and acidic effects)

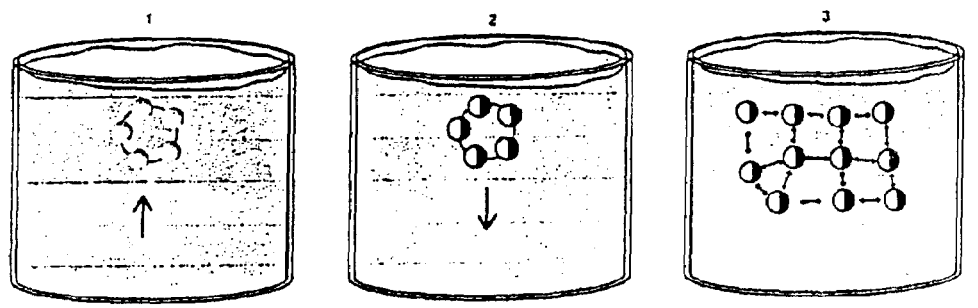

Untreated fat particles in aqueous liquid

Impeded fat particles with E 444 or E 445 in aqueous liquid homogenised, impeded and stabilised fat particles with E 444 or E 445 and E 414 or E 1450 in aqueous liquids Inversion, phase separation (fat/water) on heating and after the addition of hydrochloric acid (gastric juice/gastric acid)

WATER FREE UBIQUINONE CONCENTRATE

This is a nationalization of PCT/EP02/07195 filed Jun. 29, 2002 and published in German.

1 Introduction

Substances such as coenzyme $Q_{10}$, tocopherol, isoflavone, vitamin A, etc., are lipophil, and as opposed to water soluble substances, such as ascorbic acid, they are bio-available only in small amounts, and furthermore can be used in the classical food area only with large limitations for technological reasons. The following explanations serve to illustrate these facts.

In order to recreate the advantages of water soluble coenzyme $Q_{10}$, the mechanisms of lipid digestion and emulsions (fat-water mixtures) that provide no advantages in lipid digestion, should be investigated further.

1.1 Lipid Digestion

Nutrition has the meaning and purpose that life-essential nutrients, such as vitamins, minerals, trace elements, are absorbed and utilized by the body. The absorption of these substances is performed by the mucous membrane cells in the small intestine.

The cells of the small intestine, for example, are covered with a microscopically fine water film so that the cells can directly absorb only such substances that are soluble in this water film. The bio-availability of water soluble substances, such as sugar, salts, and certain vitamins (for instance vitamin C) is therefore at an optimum.

However, fat soluble substances—such as commonly available coenzyme $Q_{10}$, and vitamins E and A—are unable to penetrate the water film, but instead must be "pre-treated" in the small intestine. This occurs by means of micelle formation with the aid of bile salts. This micelle formation step is the reason that the absorption of fatty substances cannot occur as easily as for water soluble substances. This disadvantage is evident from the following facts:

1. The micelle formation in the small intestine occurs at a time delay, or after the release of bile secretion (bile juice) and enzymes of the pancreas.
2. The micelle formation that is considered the prerequisite for fat digestion absorb only part of the fatty substances received with food.
3. During the comparatively long lasting formation and "eating" of micelles in the small intestine, the rest of the digestive processes (transport, etc.) continue without interruption so that the micelles formed, which contain the fat particles, are discharged largely undigested.

The facts described explain the very low bio-availability of fat soluble substances, which is at approximately 25 percent. To the consumer this means that he/she discharges a large part of the fat soluble substances absorbed with food or nutritional supplements, such as fat soluble coenzyme $Q_{10}$ capsules, unutilized. Furthermore, some people are unable to absorb fat soluble substances due to certain metabolic diseases—unless they are present in water soluble form (see attached expert statement by Prof. Biesalski).

1.2 Emulsions

Emulsions are turbid oil-water mixtures that provide no advantages for fat digestion whatsoever. They have the characteristic features of lipids and oils, or fat soluble substances (such as coenzyme $Q_{10}$). These compounds are often lighter than water, and therefore float to the surface in aqueous liquids as well as in gastric juices. At the same time, they arrange themselves next to one another due to their hydrophobic interaction, and form larger formations due to this agglomeration or coagulation (FIG. 2).

In the large-technical production of emulsions, fat soluble compounds, such as vitamins E and A, are treated with beta-acetate isobutyrate (SAIB, E 444), or glycerine ester from root resin (E 445), in order to increase the specific weight of the lipid soluble compounds. This ensures that the lipid or oil particles do not rise to the surface in an aqueous medium. Subsequently, the stabilizer rubber arabicum (Arabic rubber, E 414), or modified starch (E 1450) is added. This avoids the lipid or oil particles flowing together into larger formations (droplets). In the following step, the lipid and oil particles are then crushed to a size of approximately 1 μm by means of homogenisation (FIG. 2).

The emulsion is gained by means of the described process—an turbid oil-water mixture that is initially stable in its packaging. However, with its consumption, it is "destroyed" in the stomach, i.e. phase separation occurs, so that it provides no advantages whatsoever for the digestion of the emulsified lipids or oils. These facts become evident in the following test:

When the (turbid) emulsion is heated to body temperature, and gastric juices (hydrochloric acid) are added, a visible separation into a watery and a fatty phase occurs immediately. The end result is that emulsions do not provide water solubility of lipids.

BRIEF DESCRIPTION OF THE DRAWINGS

FIG. 2 shows a diagram of the process for making an emulsion and its reversal by heat and acid effects.

Figure 1:
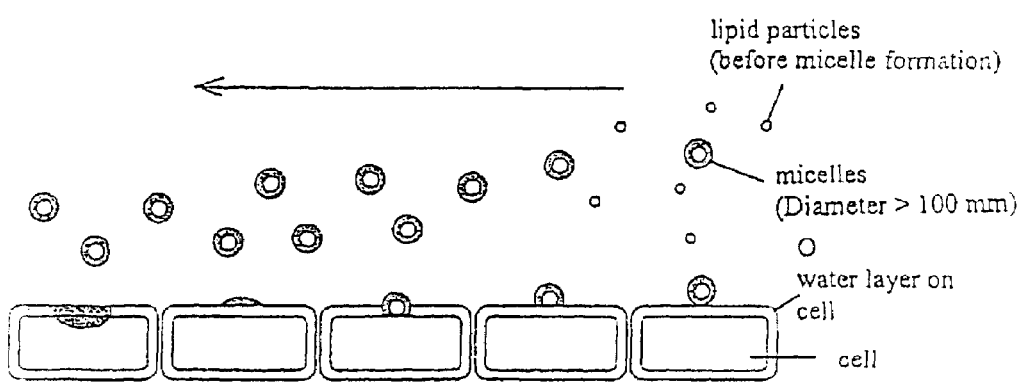
FIG. 1 is a schematic illustration of the absorption of lipids by the cells of the small intestine.
Figure 3:
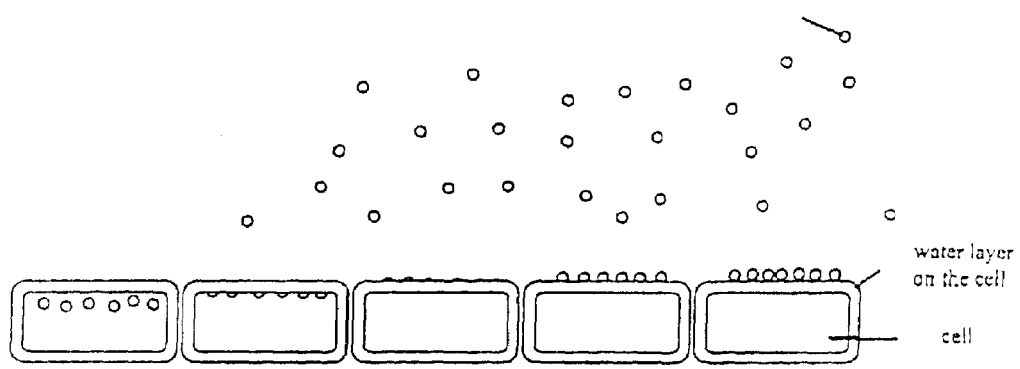
FIG. 3 is a schematic illustration of the absorption of water soluble variations of originally lipid soluble substances through the mucous membrane cells of the small intestines after the use of the claimed process.
Figure 4:
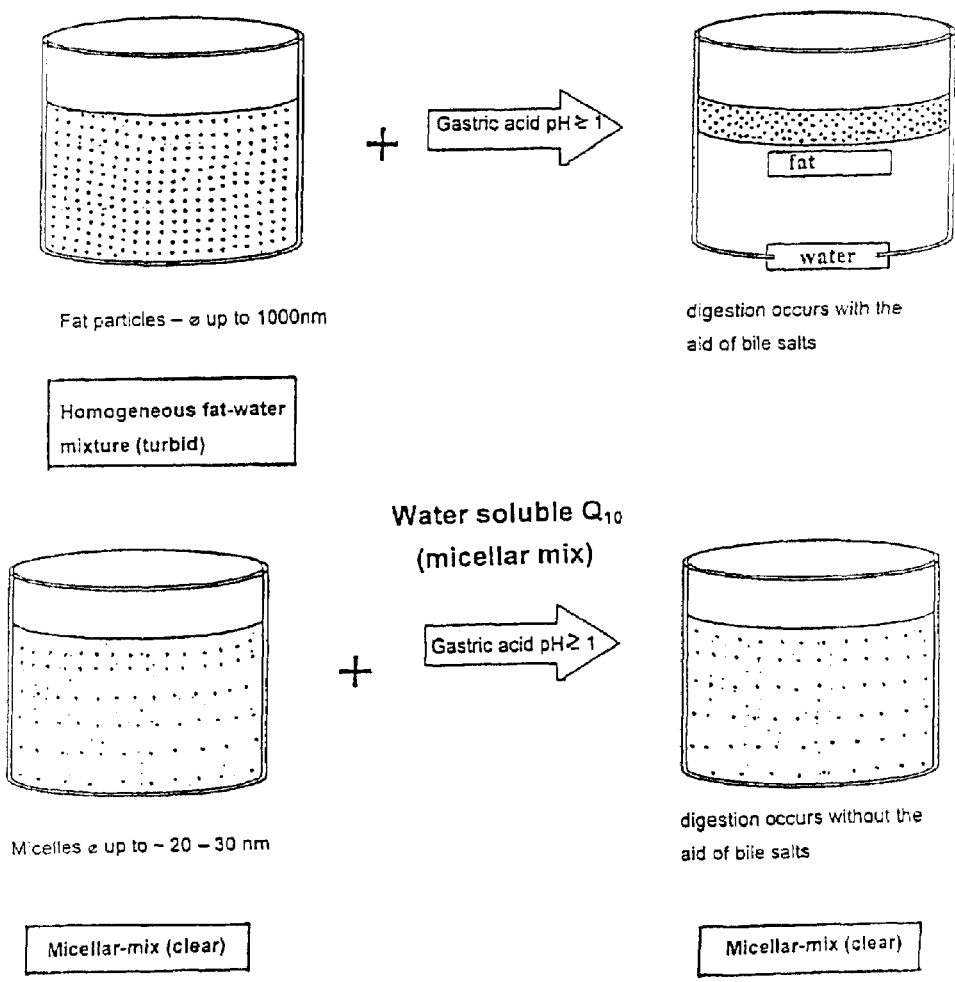
FIG. 4 is a schematic illustration of the difference in digestion when comparing the prior art emulsion to the micellar-mix of the present invention.

1.3 The Revolutionary Optimization of Bio-availability of Fat Soluble Substances by Transformation into their Water Soluble Variations Absorption and utilization (digestion) of lipids require the formation of micelles in the intestine so that the lipids can penetrate the cell like water soluble substances. If the micelles are already present in the product at a size of approximately 50 nm, and are additionally stable thermally and in gastric acids, the endogenic process of micelle formation is redundant. In this case, the lipids, such as coenzyme $Q_{10}$, are completely absorbed by the body from these micelles just like water soluble substances.

Among others, the water soluble coenzyme $Q_{10}$ was developed according to this principle. As opposed to emulsions, solubilisates of the water soluble coenzyme $Q_{10}$ show exactly the same characteristics as water soluble substances. The coenzyme solubilisate $Q_{10}$ is absolutely clear, and remains absolutely stable thermally and in acids even at 100° C., and at a pH 1 value. The four times higher and quicker bio-availability is ascribed to these facts.

The micelle-shaped units that are already present in the product, which contain the lipids (such as coenzyme $Q_{10}$), are stable with respect to temperature and acid effects in the stomach. They reach the small intestine unharmed, attach themselves to the mucous membrane cells across their entire surfaces, and can be easily absorbed, leading to a therefore four times faster bio-availability, by the cell, than is the case for a "normal" fat digestion.

For the consumer, this fact means an economic advantage on the one hand, and on the other hand the sureness that what he/she is taking will be effective.

2 The Special Advantages of the Invention to be Patented

The formation of micelles is absolutely crucial, and an indispensable prerequisite for the digestion, or for the cellular lipid resorption. It occurs either with the aid of bile salts and enzymes in the small intestine, or according to the invention described herein, already within the product. The product micelles carrying the active substance and formed according to the invention must meet the following conditions in order not to be treated by the digestive tract as fat soluble, but instead as water soluble substances so that a special micelle formation is no longer necessary in the small intestine.

1. A size that is as small as possible:
   The smaller the micelles are in the product, the lower the turbidity.
2. Stability in gastric acid
3. Long-term stability within the product:
   The long-term stability within the product is given only if the coenzyme $Q_{10}$ does not crystallize after a long storage period, and remains transparent at 37° C.

The water-free water soluble coenzyme $Q_{10}$ concentrate offers consumers the advantages of two fundamental new developments in one single product with the use in capsules—particularly in gelatine-free capsules (VegaGel):

a) The cosmetics industry is provided with the possibility to produce a skin care product, in which the valuable coenzyme $Q_{10}$ is actually absorbed by the skin cell. It was shown what kind of problems the absorption of fat soluble substances creates in the digestive tract due to micelle formation. This problem is even substantially larger in the penetration of fat soluble substances through the skin, because it lacks an endogenic micelle formation, which would make a measurable absorption of, for instance, coenzyme $Q_{10}$ possible.

Therefore, water soluble coenzyme $Q_{10}$ offers incomparably better utilization possibilities to the cosmetic branch.

b) The beverage industry is provided with the large technical advantage that water soluble coenzyme $Q_{10}$ is optimally suited for the production of clear beverages with a high attractivity, and enormous additional uses (U.S. patent specification No. 6,048,566).

However, the concentrate described here is less suitable for the supplementation in capsules, or other forms of administration due to its high water content.

The invention is therefore based on the sense and purpose of developing a highly concentrated, i.e., three-percent water-free coenzyme Q10 concentrate that is transparent and water soluble at room or body temperature (without additional heating), and is therefore technologically better processable and is also better bio-available for capsules or comparative forms of administration, as well as for cosmetics etc.

For this purpose, the invention includes a water soluble, essentially water-free ubiquinone concentrate that has an emulsifier with an HLB value between 9 and 16, the ubiquinone $Q_{10}$, as well as a light oil with a high content of triglyceride. As the emulsifier, polysorbate 80 is particularly recommended. As light oil, particularly vegetable oils with a high content of triglycerides, such as α-linolenic acid, γ-linolenic acid, linoleic acid, oleic acid, are suitable. Safflower oil, for instance, contains up to 83% linoleic acid, and up to 24% oleic acid. Linseed oil, which can also be used for the inventive purpose, contains up to 71% linolenic acid, up to 31% linoleic acid, and up to 23% oleic acid. Sunflower oil, soy oil, and olive oil contain respective components so that these oils may also be used as the light oils for the invention. Additional purposeful characteristics of the inventive concentrate are stated in the sub-claims.

The concentrate mentioned can be produced according to the invention in such a way that coenzyme Q 10 is added to an emulsifier with an HLB value between 9 and 16 that is heated to a temperature of approximately 60° C.

The mixture is stirred at the elevated temperature until it becomes homogeneous and transparent. Subsequently, a light oil is heated to the elevated temperature and added to the mixture, and this second mixture is stirred at the elevated temperature until it becomes homogeneous and transparent as well. Afterwards, this second mixture can be cooled down to room temperature. Additional preferred processing steps of the inventive method are stated in the additional sub-claims.

In addition to the possibility of a direct application of the new product in capsules or comparative forms of distribution, and in cosmetics, etc., the new product provides the advantages—as opposed to aqueous variations—that the reaction and therefore the rate of decomposition can be reduced in the product due to its viscous characteristics, and that no sediment, or residue is formed even after a longterm storage. By adding the oils mentioned, a possible crystallization in the concentrate at body temperature is effectively avoided. Therefore, the present invention is a substantial improvement of the U.S. Pat. No. 6,048,566, where the undiluted and water-free base concentrate is only water soluble at a temperature above 45° C., i.e. a much higher temperature than body temperature (37° C.).

For the purpose of further explanation of the invention, a few production examples for the concentrate are described in the following:

PRODUCTION EXAMPLE 1

Material: 1) 30 g of pure coenzyme $Q_{10}$ (yellow powder)
2) 820 g of an emulsifier with an HLB value between 9 and 16, preferably polyoxyethylene-sorbitane monooleate (polysorbate 80, lamesorb SMO 20)
3) 150 g of safflower oil, or a comparable vegetable oil Method: 820 g of emulsifier with an HLB value between 9 and 16, preferably polysorbate 80, is heated to approximately 85 DC. 30 g of pure coenzyme $Q_{10}$ (yellow powder) is then added, and the mixture (total amount 850 g) is stirred while maintaining the temperature of approximately 85° C. (about 5 minutes) until it has become homogeneous and transparent. Subsequently, 150 g of safflower oil heated to 85° C., or a comparable vegetable oil, is added to this mixture, which is stirred at approximately 85° C. (about 2 minutes) until the entire mixture (1,000 g) has become homogeneous and transparent. After cooling to room or body temperature, clarity and water solubility remain intact.

Turbidity: The turbidity measurement was performed using the Turb 550, or the Turb 550 IR by WTW company, and follows the recommendations of the US EPA, or corresponds to ISO 7027/DIN 27027. The turbo measurement of the previously mentioned mixture with water to a 0.01-percent dilution, which corresponds to 100 mg of coenzyme $Q_{10}$ per liter (three times the RDA) resulted in a value of -continued 3.0 ± 0.2 at room temperature on a scale from 1 to 1,000. The measured substance is considered clear at values between 1.0 and 10.0.

| | |
|---|---|
| Material: | 1) 50 g of pure coenzyme Q 10 (yellow powder)<br>2) 790 g of the emulsifier polysorbate 80<br>3) 160 g of safflower oil |
| Method: | 750 g of polysorbate 80 is heated to approximately 85° C. 50 g of coenzyme Q 10 is then added, and the mixture (840 g) is stirred maintaining the temperature of approximately 85° C. (about 5 minutes) until it has become homogeneous and transparent. Subsequently, 160 g of safflower oil heated to 85° C. is added to this mixture, still maintaining the temperature of approximately 85° C. (about 2 minutes) until the entire mixture (1,000 g) has become homogeneous and transparent. After cooling to room or body temperature, clarity and water solubility remain intact. |
| Turbidity: | The turbidity measurement was performed as stated in example 1, whereby again a 0.01-percent dilution with water of the previously mentioned mixture was used. This resulted in a value of 5.0 +/− 0.2 at room temperature on a scale of 1 to 1000, which states clarity. |

PRODUCTION EXAMPLE 2

| | |
|---|---|
| Material: | 1) 30 g of pure coenzyme $Q_{10}$ (yellow powder)<br>2) 730 g of an emulsifier with an HLB value between 9 and 16, preferably polyoxyethylene-sorbitane monooleate (polysorbate 80, Lamesorb SMO 20)<br>3) 140 g of safflower oil, or a comparable vegetable oil<br>4) 100 g of glycerin |
| Method: | 730 g of an emulsifier with an HLB value between 9 and 16, preferably polysorbate 80, is heated to approximately 85° C. 30 g of pure coenzyme $Q_{10}$ (yellow powder) is then added, and the mixture (total amount 760 g) is stirred while maintaining the temperature of approximately 85° C. (about 5 minutes) until it has become homogeneous and transparent. Subsequently, 140 g of safflower oil, and 100 g of glycerin, both heated to approximately 85° C., are added to this mixture. Maintaining the temperature of approximately 85° C. the mixture is stirred (about 2 minutes) until the entire mixture (1,000 g) has become homogeneous and transparent. |
| Turbidity: | The turbidity measurement was performed using the Turb 550, or the Turb 550 IR by the WTW company, and follows the recommendations of the US EPA, or corresponds to ISO 7027/DIN 27027. The mixture described above mixed with water to a 0.01-percent dilution, which corresponds to 100 mg of coenzyme $Q_{10}$ per liter (three times the RDA), resulted in a value for turbidity of 4.0 ± 0.2 at room temperature on a scale of 1 to 1,000. The measured substance is considered clear at values between 1.0 and 10.0. |

PRODUCTION EXAMPLE 3

For a lower Q 10 concentration as described in the production example 3, an appropriate lower concentration of the emulsifier can be used. The water-free glycerin added here serves for filling the mixture to 1,000 g. Of course, other water-free filling materials may also be used.

The recommendation for the production of five-percent water soluble coenzyme $Q_{10}$ concentrates is justified as follows:

1) a coenzyme $Q_{10}$ concentration above five percent bears the risk of a crystallization of the coenzyme $Q_{10}$, which could compromise or degrade the water solubility of the concentrate.
2) A coenzyme $Q_{10}$ concentration below three percent would result in the fact that a larger concentrate amount would be necessary to meet the daily requirement with a correspondingly higher volume, which would, however, be too large for the processing in capsules.

One gram of the three-percent water soluble coenzyme $Q_{10}$ concentrate contains 30 mg of coenzyme $Q_{10}$. This amount corresponds to the daily requirement, and can be processed in capsules, as far as volume is concerned.

Based on the far better bio-availability of the water soluble coenzyme $Q_{10}$ concentrate, only half of the presently recommended RDA is necessary, i.e., 15 mg of coenzyme $Q_{10}$ in water soluble form (variation according to the invention). This coenzyme $Q_{10}$ amount (15 mg) is contained in 500 mg of the water soluble concentrate.

One capsule, which contains 500 mg of water soluble coenzyme $Q_{10}$ concentrate according to the production example 3 with 15 mg of coenzyme $Q_{10}$, also contains a lower amount of the emulsifier polyoxyethylene-sorbitane monooleate (polysorbate 80, lamesorb SMO 20). Product technologically seen, there are no limitations to the added amount of the emulsifier polyoxyethylene-sorbitane monooleate. The rule "quantum satis" applies.

The concentrates created according to the preceding production examples 1 to 3 will become creamy and intransparent after cooling to room temperature. Once heated to body temperature, the concentrate will become transparent, (viscous) fluid, and easy to mix with slightly heated water (approximately 37° C.). The mixture of these concentrates with clear water will result in a completely clear, stable, and gastric acid resistant solution, in which the contained coenzyme $Q_{10}$ is included in the form of micelle-like units, which a) are absorbed four times faster, and quantitatively better in the small intestine just like water soluble substances without the participation of bile salts, and b) which make it possible for the first time that an originally fat soluble substance penetrates deeper layers of the skin in a larger amount (in the cosmetic area).

In addition to capsules, the concentrates created according to the preceding production examples 1 to 3, can be processed in soft and/or hard gelification as a laminate and/or filling in various food items, such as chocolate, chewing gum etc. In undiluted, but preferably in diluted form, the described concentrates can be packaged into drip bottles or drinking ampules. Furthermore, the concentrates can be added to dental care and cleaning products (toothpaste).

The invention claimed is:

1. A water soluble, essentially water-free ubiquinone concentrate comprising ubiquinone $Q_{10}$, a light oil containing triglycerides, and an emulsifier with an HLB value between 9 and 16, which emulsifier is a polysorbate and is present in a content of at least about 73 weight % of the total weight of the concentrate.

2. Concentrate according to claim 1 wherein polysorbate 80 is the polysorbate.

3. Concentrate according to claim 1, wherein the $Q_{10}$ content is about 3 weight % to about 5 weight %.

4. Concentrate according to claim 3 wherein the light oil is selected from the group consisting of safflower oil, linseed oil, soy oil, and sunflower oil.

5. Concentrate according to claim 4 with a safflower oil content of about 8 weight % to about 20 weight %, preferably of about 12 weight % to about 15 weight %.

6. Concentrate according to claim 4 additionally comprising one or more water-free fillers, such as glycerin.

7. Concentrate according to claim 3 having a filler content of up to approximately 35 weight %.

8. Concentrate according to claim 4 having a filler content of up to approximately 35 weight %.

9. Concentrate according to claim 3 additionally comprising a thickener, such as gelatin and/or pectin and/or agar-agar and/or gum arabic.

10. Capsule to be applied orally, with a particularly gelatin-free shell, which contains a concentrate according to claim 1.

11. Skin care product with the addition of a concentrate according to claim 1.

12. Dental care product with the addition of a concentrate according to claim 1.

13. Method for the production of a concentrate according to claim 1, wherein pure coenzyme $Q_{10}$ is added to a polysorbate, said polysorbate present in a content of at least about 73 weight % of the total weight of the concentrate, and said polysorbate having been heated to temperature of over approximately 60° C., and stirred at said temperature until the mixture has become homogeneous and transparent, subsequently adding to the mixture a light oil, and having been heated to a temperature of over approximately 60° C., and stirring this second mixture at said temperature until it has become homogeneous and transparent, and thereafter cooling the second mixture down to room temperature.

14. Method according to claim 13, wherein the elevated temperature is a temperature of approximately 85° C.

15. Method according to claim 13, wherein the light oil, such as safflower oil and/or linseed oil and/or soy oil and/or sunflower oil, is added to the second mixture.

16. Method according to claim 15, wherein polysorbate 80 is used as the polysorbate.

17. Method according to claim 13, characterized in that one or more water-free fillers that have been heated to the elevated temperature are added to the second mixture.

18. Method according to claim 17, characterized in that glycerin is chosen as the filler.

19. Method according to claim 13, characterized in that the emulsifier, the ubiquinone, and the light oil are used in such quantities that the second mixture has an emulsifier content of about 73 to about 85 weight %, an ubiquinone content of about 3 weight %, and the content of the light oil is about 8 weight % to about 20 weight %, preferably of about 12 weight % to about 15 weight %.

20. Method according to claim 17, characterized in that the fillers are added at up to about 35 weight %.

21. Method according to claim 13, characterized that a thickener that is approximately in the form of gelatin and/or pectin and/or agar-agar and/or gum arabic, is added to the second mixture.

22. Method according to claim 15, wherein a quantity of about 8 weight % to about 20 weight % of the light oil is added to the second mixture.

23. Method according to claim 13, wherein a quantity of about 3 weight % to about 5 weight % of $Q_{10}$, is added.

* * * * *